United States Patent [19]

Sorrentino

[11] Patent Number: 4,892,877

[45] Date of Patent: Jan. 9, 1990

[54] ANTITUSSIVE LIQUID COMPOSITIONS CONTAINING PHENOL

[75] Inventor: James V. Sorrentino, Wilton, Conn.

[73] Assignee: Richardson-Vicks Inc., Shelton, Conn.

[21] Appl. No.: 112,922

[22] Filed: Oct. 27, 1987

[51] Int. Cl.[4] .......................................... A61K 31/485
[52] U.S. Cl. .................................... 514/289; 514/731; 514/849; 514/850
[58] Field of Search ................ 514/289, 731, 849, 850

[56] References Cited

U.S. PATENT DOCUMENTS

| 4,212,878 | 7/1980 | Lednicer et al. | 514/210 |
|---|---|---|---|
| 4,372,942 | 2/1983 | Cimiluca | 514/289 |
| 4,374,146 | 2/1983 | Phillips | 514/466 |
| 4,446,140 | 5/1984 | Nelson | 514/289 |
| 4,636,520 | 1/1987 | Umio et al. | 514/399 |

OTHER PUBLICATIONS

Physician's Desk Reference for Non-Prescription Drugs, 17th Ed., (1962).
Physicians' Desk Reference for Non-prescription Drugs, 8th Ed., 1987, pp. 654–655.
Federal Register, vol. 41, No. 176, pp. 22776–22777, (1982).

Primary Examiner—H. M. S. Sneed
Assistant Examiner—J. Saba
Attorney, Agent, or Firm—David K. Dabbiere; Douglas C. Mohl; Jack D. Schaeffer

[57] ABSTRACT

Novel antitussive and anesthesic liquid compositions of matter for oral use comprising an effective oral antitussive drug and phenol, and method of using same.

7 Claims, No Drawings

ANTITUSSIVE LIQUID COMPOSITIONS CONTAINING PHENOL

BACKGROUND OF THE INVENTION

This invention is directed to improved antitussive swallowable liquid compositions for oral use. Oral cough preparations, such as syrups, solutions, suspensions and the like, containing an effective antitussive agent have long been used for the symptomatic relief of coughs. The most popular of such preparations contain either dextromethorphan or its hydrobromide salt or codeine or its sulfate salt as the active antitussive agent.

Phenol is a known topical anesthetic, which has been used to treat minor sore mouth and sore throat pain. The mode of action, fast acting but not long lasting, is that it desensitizes sensory nerve receptors present in the mucous membranes of the throat and oral cavity to exert its local anesthetic effect. Previous dosage forms of administration have included aqueous solutions of 1.4% phenol for use as a mouthwash, rinse or gargle, which is expelled from the oral cavity after use, and as a throat spray. Such forms provide topical application of an effective dose of phenol directly to the mucous membranes or mouth tissues. The ensuing anesthesia/analgesia lasts so long as an effective concentration of the phenol is supplied to the site of action. As the phenol is washed away, e.g., by saliva, the anesthetic/analgesia action recedes.

Solid lozenge forms of the antitussive agent, dextromethorphan hydrobromide (10 mg), and phenol (32.5 mg) are known to be commercially available in Canada for the respective systemic treatment of coughs and local treatment of accompanying irritated throat. Also in British Patent No. 1,144,915, medicinal two-phase solid pastille forms containing (among others) dextromethorphan and phenol in the separate phases are disclosed for the respective treatment of cough and sore throat relief. Such solid lozenge and pastille forms require the action of saliva over an extended period of time for dissolution of the solid form, thereby effectuating release of the respective active ingredients and prolonged contact of phenol at the mucosal membrane throat site.

To date, however, applicants herein are unaware of any combination of an effective oral antitussive drug and phenol in a liquid composition for administration by immediate swallowing.

It has now been found that the combined use of phenol and an oral antitussive drug in a swallowable liquid provides improved relief to an individual afflicted with cough or cough and associated sore throat, without the aforementioned need for prolonged contact with mucosal membranes of the throat and oral cavity.

DESCRIPTION OF THE INVENTION

More specifically, the subject invention provides a liquid pharmaceutical composition of matter for the treatment of cough or cough and associated sore throat in a human afflicted with same. Said composition comprises, per dose of 5-30 milliliters, an aqueous-based orally acceptable pharmaceutical carrier, an effective antitussive swallowable amount of an oral antitussive drug, and from about 10 to about 150 milligrams (mg), and preferably from about 50 to about 150 mg, of phenol, said composition having a pH of about 6-9.

As used herein, the term "oral antitussive drug" means a drug that is taken by mouth and acts systemically to relieve cough (see Federal Register, Vol. 52, No. 155, 12 August 1987, page 30055).

The choice of a particular oral antitussive drug is not critical. Well recognized oral antitussive drugs include, but are not limited to, for example, the non-narcotic type such as dextromethorphan and its acid addition salts, preferably the hydrobromide, chlophendianol hydrochloride, carbetapentane citrate, caramiphen edisylate, diphenhydramine and its hydrochloride salt, noscapine hydrochloride and the like, and the non-addictive narcotic type such as codeine and its sulfate or phosphate salts, hydrocodone and its bitartrate salt, hydromorphone hydrochloride, and the like. The usual adult dosage for such antitussives, which may also be utilized per dose in the subject compositions, are indicated in Table I.

TABLE I

| Oral Antitussive Drug | Usual Adult Dose (mg) |
|---|---|
| Dextromethorphan HBr | 10-30 |
| Chlophedianol HCl | 15-25 |
| Carbetapentane citrate | 15-30 |
| Caramiphen edisylate | 15-20 |
| Noscapine HCl | 15-30 |
| Diphenhydramine HCl | 15-25 |
| Codeine sulfate | 10-20 |
| Hydrocodone bitartrate | 5-10 |
| Hydromorphone HCl | 2 |

The highly advantageous properties of the compositions of this invention are demonstrated by their improved anti-cough effectiveness, for example, by the method of E. W. Packman and S. J. London described in Current Therapeutic Research, Vol. 21, No. 6, June 1977, page 855. The methodology involves the quantitative measurement of the effect of an antitussive preparation on cough artificially induced in normal healthy subjects by a citric acid aerosol at various intervals.

The subject compositions surprisingly provide marked anti-cough effectiveness and also provide fast-acting and effective relief of accompanying irritated sore throat even though the subject composition is swallowed in the normal fashion, as opposed to the heretofore usage of phenol locally over a period of time, for example, by means of a spray, gargle, lozenge and the like. It is surprisingly found that, by the simple act of completely swallowing the subject composition, which provides minimal contact time with the mucosal membranes of the throat and oral cavity, the therapeutic anesthetic effect of phenol is still exerted promptly.

The present invention thus provides a method of treating cough or cough and associated sore throat in a human afflicted with said symptoms comprising the oral administration to said human, by direct swallowing, of at least one 5-30 ml dose of a liquid pharmaceutical composition having a pH of about 6-9 comprising, per 5-30 ml dose, water, an effective antitussive amount of an oral antitussive drug, from about 50 to about 150 milligrams of phenol, and, preferably, from about 5 to about 25 volume percent of ethyl alcohol.

Since many of the oral antitussive drugs are generally used in the form of a water soluble salt, they can be readily incorporated into conventional aqueous-based cough syrups and solution formulations. Water insoluble or difficultly soluble antitussives, generally in base form, may also be incorporated into aqueous-base orally acceptable pharmaceutical carriers such as dispersions, suspensions, oil-in-water emulsions and the like by means of suitable dispersing, suspending or emulsifying agents, respectively, which are readily apparent to those skilled in the art of pharmaceutical formulations.

In preparing the pharmaceutical compositions of the present invention, the oral antitussive drug and phenol components are incorporated into an aqueous-based orally acceptable pharmaceutical carrier consistent with conventional pharmaceutical practices. An "aqueous-based orally acceptable pharmaceutical carrier" is one wherein the entire of predominant solvent content is water. Typical carriers include simple aqueous solutions, syrups, dispersions and suspensions, and aqueous based emulsions such as the oil-in-water type. The most preferred carrier is the commonly used syrup form, an aqueous solution of high sugar content. While the amount of water in the compositions of this invention can vary over quite a wide range depending upon the total weight and volume of the two essential active ingredients and other optional non-active ingredients, the total water content, based on the weight of the final composition, will generally range from about 20 to about 75%, and, preferably, from about 20 to about 40%, by weight/volume.

Although water itself may make up the entire carrier, typical cough formulations preferably contain a co-solvent, for example, ethyl alcohol, propylene glycol, glycerin and the like, to assist solubilization and incorporation of water insoluble ingredients, flavoring oils and the like into the composition. In general, therefore, the compositions of this invention preferably contain from about 5 to about 25 volume percent and, most preferably, from about 10 to about 20 volume/volume percent, of the co-solvent.

To provide and maintain the subject compositions at a pH of from about 5 to about 9 and preferably from about 6 to about 7, buffers consistent with conventional pharmaceutical practices are generally utilized such as, for example, sodium citrate buffer, sodium phosphate buffer, and the like.

The compositions of this invention may optionally contain one or more other known therapeutic agents, particularly those commonly utilized in cough/cold preparations, such as, for example, a decongestant such as pseudoephedrine hydrochloride, phenylephrine hydrochloride and ephedrine hydrochloride; an analgesic such as acetaminophen and ibuprofen; an expectorant such as glyceryl guaiacolate, terpin hydrate and ammonium chloride; and an antihistamine such as chlorpheniramine maleate, doxylamine succinate, brompheniramine maleate and diphenhydramine hydrochloride.

Other optional ingredients well known to the pharmacist's art may also be included in amounts generally known for these ingredients, for example, natural or artificial sweeteners, flavoring agents, colorants and the like to provide a palatable and pleasant looking final product; antioxidants, for example, butylated hydroxy anisole or a butylated hydroxy toluene and preservatives, for example, methyl or propyl paraben or sodium benzoate to prolong and enhance shelf life.

The following examples illustrate embodiments of the subject invention wherein both essential and optional ingredients are combined.

Example 1

| Ingredients | Amount/10 ml Dose |
| --- | --- |
| Invert syrup, medium | 8.5 g |
| Sodium citrate, hydrous | 200.0 mg |
| Sodium benzoate | 10.0 mg |
| Absolute alcohol | 1.00 ml |
| Propylene glycol | 1.16 g |
| Phenol | 75.0 mg |
| Dextromethorphan HBr | 30.0 mg |
| Chlorpheniramine maleate | 4.0 mg |
| Colorant | 207.0 mg |
| Flavorants | 60.55 mg |
| Purified water, q.s. ad (pH = 6.6) | 10.00 ml |

Example 2

| Ingredients | Amount/15 ml Dose |
| --- | --- |
| Liquid sugar (66% sucrose in water) | 12.0 g |
| Sodium benzoate | 15.0 mg |
| Sodium citrate, hydrous | 300.0 mg |
| Citric acid, anhydrous | 4.11 g |
| Sodium saccharin | 30.00 mg |
| Propylene glycol | 2.25 g |
| Dextromethorphan HBr | 30.00 mg |
| Pseudoephedrine HCl | 60.00 g |
| Absolute alcohol | 1.50 ml |
| Phenol | 112.50 mg |
| Guaifenesin | 200.00 mg |
| Menthol | 22.50 mg |
| Colorant | 5.1 mg |
| Flavorants | 82.55 g |
| Purified water, q.s. ad (pH = 7.0) | 15.00 ml |

Example 3

| Ingredients | Amount/15 ml Dose |
| --- | --- |
| Liquid sugar | 12.00 g |
| Sodium benzoate | 15.00 mg |
| Sodium citrate, hydrous | 300.00 mg |
| Citric acid, anhydrous | 4.11 mg |
| Sodium saccharin | 30.00 mg |
| Propylene glycol | 2.25 g |
| Dextromethorphan HBr | 30.00 mg |
| Absolute alcohol | 1.50 ml |
| Phenol | 150.00 mg |
| Colorant | 0.045 ml |
| Flavorant | 0.015 ml |
| Purified water, q.s. ad (pH - 7.0) | 15.00 ml |

Example 4

| Ingredients | Amount/5 ml Dose |
| --- | --- |
| Liquid sugar | 4.0 g |
| Sodium benzoate | 5.0 mg |
| Sodium citrate, hydrous | 100.0 mg |
| Citric acid, anhydrous | 1.37 mg |
| Sodium saccharin | 10.00 mg |
| Propylene glycol | 750.0 mg |
| Carbetapentane citrate | 30.0 mg |
| Absolute alcohol | 0.50 ml |
| Phenol | 10.0 mg |
| Flavorant | 18.0 ml |
| Colorant | 2.5 mg |
| Purified water, q.s. ad | 5.0 ml |

Example 5

| Ingredients | Amount/30 ml Dose |
| --- | --- |
| Liquid sugar | 24.0 g |
| Sodium benzoate | 30.0 mg |
| Sodium citrate, hydrous | 600.0 mg |
| Citric acid, anhydrous | 8.22 mg |
| Sodium saccharin | 60.00 mg |
| Propylene glycol | 4.5 g |
| Codeine sulfate | 15.0 mg |
| Absolute alcohol | 3.00 ml |
| Phenol | 50.0 mg |
| Flavorant | 108.0 mg |
| Colorant | 15.0 mg |
| Purified water, q. s. ad | 30.0 ml |

I claim:

1. A liquid pharmaceutical composition of matter for use in the treatment of coughs and associated sore throat, by direct swallowing, comprising, per 5–30 ml dose:
   (a) an aqueous-based orally acceptable pharmaceutical carrier;
   (b) an effective antitussive amount of dextromethorphan hydrobromide;
   (c) from about 10 to about 150 milligrams of phenol; and
   (d) from about 5 to about 25 volume/volume percent of co-solvent; said composition having a pH of about 5–9.

2. The composition of claim 1 wherein said co-solvent in (d) is a member selected from the group consisting of ethyl alcohol, glycerin and propylene glycol.

3. The composition of claim 2 wherein (a) is from about 20 to about 40% by weight of water.

4. A method of treating cough or cough and associated sore throat in a human afflicted with same which comprises orally administering to said human, by direct swallowing, of at least one 5–30 ml does of a liquid pharmaceutical composition of matter comprising, per 5–30 ml dose:
   (a) an aqueous-based orally acceptable pharmaceutical carrier;
   (b) an effective antitussive amount of dextromethorphan hydrobromide;
   (c) from about 10 to about 150 milligrams of phenol; and
   (d) from about 5 to about 25 volume/volume percent of co-solvent; said composition having a pH of about 5–9.

5. The method of claim 4 wherein said co-solvent in (d) is a member selected from the group consisting of ethyl alcohol, glycerin and propylene glycol.

6. A method of treating colds and associated sore throat in a human afflicted with same which comprises orally administering to said human, by direct swallowing, of at least one 5–30 ml dose of a liquid pharmaceutical composition of matter comprising, per 5–30 ml dose:
   (a) from about 20 to about 75% of water by weight/volume;
   (b) an effective antitussive amount of dextromethorphan hydrobromide;
   (c) from about 50 to about 150 milligrams of phenol; and
   (d) from about 10 to about 20 volume percent of ethyl alcohol; said composition having a pH of about 6–7.

7. The method of claim 6 wherein (a) is from about 20 to about 40% by weight of water.

* * * * *